United States Patent
Lee et al.

(10) Patent No.: US 8,250,729 B2
(45) Date of Patent: Aug. 28, 2012

(54) 3D FABRICATION OF NEEDLE TIP GEOMETRY AND KNIFE BLADE

(75) Inventors: Sung K. Lee, Salt Lake City, UT (US); Charles L. Thomas, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1007 days.

(21) Appl. No.: 11/818,622

(22) Filed: Jun. 14, 2007

(65) Prior Publication Data
US 2009/0099534 A1  Apr. 16, 2009

Related U.S. Application Data

(60) Provisional application No. 60/830,307, filed on Jul. 12, 2006.

(51) Int. Cl.
B21B 1/46 (2006.01)
A61M 5/32 (2006.01)

(52) U.S. Cl. ........ 29/527.2; 604/272

(58) Field of Classification Search ........ 29/527.2, 29/460; 606/272, 167, 223, 222; 264/482, 264/494; 604/272, 117, 21, 20; 430/317, 430/320

See application file for complete search history.

(56) References Cited

U.S. PATENT DOCUMENTS

| | | | | |
|---|---|---|---|---|
| 5,792,180 | A * | 8/1998 | Munoz | 606/223 |
| 6,044,566 | A * | 4/2000 | Ries et al. | 30/345 |
| 6,328,496 | B1 * | 12/2001 | Hill et al. | 401/209 |
| 7,557,325 | B2 * | 7/2009 | Fiechter | 219/121.61 |
| 2002/0082543 | A1 * | 6/2002 | Park et al. | 604/21 |
| 2002/0193754 | A1 * | 12/2002 | Cho | 604/272 |

* cited by examiner

Primary Examiner — John C Hong
(74) Attorney, Agent, or Firm — Workman Nydegger

(57) ABSTRACT

The present invention provides a method for creating a beveled needle or a blade. The method employs a side wall surface of an angled post as a base to control beveled tip geometry. The invention provides needles, microneedle arrays, blades and microblade arrays with sufficient sharpness and toughness.

22 Claims, 11 Drawing Sheets a)

b) 
Side View

Top View c)

d)

e)

a)

b)

c)

d)

e)

f)

g)

h)

i)

j)

k)

l)

m)

a)

b)

Side View

Top View c)

d)

e)

3D FABRICATION OF NEEDLE TIP GEOMETRY AND KNIFE BLADE

CROSS-REFERENCE TO RELATED APPLICATION

This application claims the benefit of the priority filing date of U.S. Provisional Application Ser. No. 60/830,307, filed Jul. 12, 2006, the contents of the entirety of which are incorporated by this reference.

TECHNICAL FIELD

The invention relates to the field of device fabrication, such as, fabrication and manufacture of microneedles or microblades.

BACKGROUND

Various forms of drug delivery systems, such as patches, capsules, and needles, are known in the art to administer drugs to a subject. Various methods of extracting blood samples, for example, making a small cut with a blade, are also available. Among the current drug delivery systems and methods of extracting blood samples, a hypodermic needle is commonly used, and is known as one of the most effective devices.

However, using a conventional hypodermic needle has several disadvantages. For example, penetration of skin using a conventional hypodermic needle may cause pain to a subject. Also, mishandling of a conventional hypodermic needle may result in infections caused by human immunodeficiency virus (HIV), hepatitis B and C viruses, etc.[1-6] Hence, many researchers have been developing hypodermic needles in small scale referred to as "microneedles," to administer drugs or extract blood.

Employing diffusion effects, a microneedle can deliver a drug through the skin without deep penetration. Skin thickness varies depending on its location. Normally, human skin comprises three layers: stratum corneum, viable epidermis, and dermis. A microneedle can penetrate the first two layers of the human skin, which is about 150 μm, to deliver a drug effectively. For collecting blood samples from a human, the length of a microneedle should be in the range of about 500 μm.

Usually, three different materials are used for creating a hollow microneedle: silicon-based material including glass, metal, and photosensitive polymers. McAllister et al. developed a hollow microneedle based on silicon dioxide ($SiO_2$), in out of plane and lateral fashion, using a heavy chemical etching process.[7-8] Stoeber et al. also applied a similar fabrication process to create a hollow microneedle.[9] Both McAllister et al. and Stoeber et al. used bulk micromachining technology to create the outer microneedle geometry, and used deep reactive ion etching (DRIE) or reactive ion etching (RIE) to create the hollow geometry. First, the process begins with the hollow holes created by the RIE technique followed by growing silicon dioxide thermally which will later become a needle structure. Machined Pyrex® is then anodically bonded to a silicon wafer to create a space for reservoir. At last, the silicon wafer is etched back with tetramethylammonium hydroxide to define the height of the needle. For lateral microneedles, it is fabricated by using a surface micromachining technique. A patterned silicon dioxide layer defines microchannels, and a nitride layer is deposited to create the top and side walls. Multiple ethylendiamminepyrocatechol (EDP) etches are carried out to complete the process.

Brazzle et al. created a metallic microneedle in a lateral fashion using surface micromachining technique.[10-11] The sequence of photolithography is carried out for patterning silicon nitride ($Si_3N_4$) on a heavily doped silicon substrate and etched in potassium hydroxide (KOH) to build a platform for the microneedle. Palladium is then electroplated on the patterned area to define the bottom wall followed by spinning a layer of photoresist. A 20 μm thick photoresist is patterned and developed to form the shape of the inside of the needle. Further electroplating is performed to build the side walls and top wall for encapsulating the photoresist. Finally, the photoresist is etched to leave a hollow metallic microneedle. McAllister et al. also manufactured a metallic microneedle array, which has square cross-section channel, using similar procedures. The base layer is electroplated followed by depositing and patterning a sacrificial thick photoresist. A seed layer is then sputtered onto the photoresist. Next, the side and top walls are electroplated. Finally, the photoresist is removed and the needle structure is lifted from the substrate.

A more realistic, out of plane, microneedle array has been developed by Kim et al. using a tapered negative photoresist (SU-8).[12] The tapered SU-8 post, which has angles between 3.1 to 5 degrees, is created using backside exposure on top of the SU-8 block which functions as a base. The seed layers are deposited, and electroplating is carried out to obtain 200 μm and 400 μm in length and thickness of 10 μm and 20 μm, respectively.

Moon et al. presented a different approach of microneedle fabrication using a deep X-ray to create an inclined polymeric microneedle.[13-14] The fabrication process begins with exposing polymethylemetacrylate (PMMA), a positive photoresist, under X-ray vertically followed by successive exposure in a pre-defined angle without moving the substrate. These two steps define a sharp needle tip at the region of interception of the exposures. A sharp tip angle below 40 degree is achieved with the needle length of between 600 μm to 1000 μm.

Kuo et al. reported fabrication of polymeric microneedles using SU-8.[15] A trapezoidal trench is created by potassium hydroxide (KOH) etch on 100 silicon wafer. The angle of the trench (about 35.3 degrees: measured from the vertical to the etched surface) is used to determine the angle of the beveled tip of a microneedle. After KOH etching is used to obtain the trapezoidal grooves, SU-8 is then applied and patterned using lithographic technique to create an array of hollow needle structures. Partial SU-8 development is carried out to expose the ends of the microneedle structure. These partially exposed needle structures are covered with another layer of SU-8 to form the base. The second SU-8 layer is further patterned and developed. The length of the microneedle is about 600 μm. A negative mold is also replicated with polydimethylesiloxane (PDMS). The report shows that these needles can successfully penetrate skin.

However, silicon-based microneedle structures tend to be brittle. Stiffness and toughness of metallic microneedles are still in question due to their thin walls. Flat needle tips of these metallic microneedles are not suitable for skin penetration. For microneedles made of photosensitive polymer, the stiffness of the needle structures and the strength between the needle structures and the bases are uncertain, even though the needles are capable of skin penetration.

Sparks et al. developed a microneedle array with sharp beveled tips using combinations of LIGA and soft lithography technique.[24] Two dimensional sawtooth profile was patterned on polymethylmethacrylate (PMMA) to create the beveled tip microneedle using Deep x-ray lithography (DXRL). The angle of the sawtooth design becomes the beveled angle of the final microneedle tip. The four different angles were tested from 25 to 40 degrees. The sawtooth structure is then cut in pieces, stacked on top of each other piece, turned, and the side wall was glued on a conductive substrate to form a 8×10 mm area for microneedle array. The second radiation performed on a glass slab to create a mask patterned of equilateral triangles with a hole pattern for defining the microneedle and the hollow features directly on the sawtooth structure. After exposure and partial development of the PMMA substrate, electroplating was carried out to form the metal layer around the needle structures. The thickness of the metal layer provides space for creating a base of the microneedle array. A successive development of the microneedle opens the bottom of the hollow features. Next, polyvinyl alcohol (PVA) is cast onto the microneedle array and used as a sacrificial template to replicate the microneedle array consisted of PMMA (material for actual microneedle structure) and a metal (for a base). Finally, PMMA is cast on the replicated PVA mold. Dissolving the PVA mold in water reveals the final product of plastic microneedle array. Advantage of the technique described above is that use of molding process opens the possibility of mass production for the beveled plastic microneedle array. The difficulty in assembly of sawtooth structure from the 2½ D in order to create 3D inclined structure, and in alignment of second radiation to create hollow features on the needle structure as well as use of expensive DXRL technique become disadvantages.

Perennes et al. created microneedle arrays and blades in plane by means of etching the patterned single crystal silicon.[25] First, the patterned single crystal silicon is etched to form the microchannels which will become the hollow structure in the needle. Second, fusion bonding of silicon to silicon is performed to seal the etched microchannels. Next, the plasma etching is carried out around the embedded microchannels according to the 2D beveled needle layout. At last, anisotropic etching creates the microneedle with the vertical side wall as well as it opens the microchannel on the side of the beveled surface along the vertical wall. In addition, the fabrication of microblade uses same manufacturing steps excluding creating microchannels and fusion bonding process. This technique can produce controllable 2½ D in plane microneedle arrays and microblades. However, the material used in the experiment is brittle and the cutter length of the blade is too short.

Although many microneedle fabrication processes have been developed, and there is a steady growth of using microneedles, the majority of the biomedical industry is still reluctant to adopt various microneedle fabrication techniques for needle production. A good needle structure should meet at least the following criteria: (1) adequate stiffness to prevent premature buckling failure, (2) adequate sharpness to penetrate a rubber-like skin, (3) adequate toughness to avoid particle breakage which may clog the vein, (4) sufficiency in length for use as a drug delivery or a body fluid extracting device, and (5) adequate biocompatibility.

SUMMARY OF THE INVENTION

Provided is, among other things, a method for preparing a needle with or without a hollow section, a needle array, a blade, or a blade array, the method comprising: creating at least one inclined or skewed structure that defines the angle of the needle or blade tip. The inclined structure can be created by various techniques including but are not limited to mechanical machining, laser ablation, lithography, abrasion, electric discharged machining (EDM), electric chemical machining (ECM) and etching. Multiple exposures can be used for creating the inclined structure. A needle or blade mold structure or an actual needle or blade structure can be built upon the inclined structure.

In certain embodiments, provided is a mold structure for a needle, a needle array, a blade or a blade array. The mold structure is built upon at least one inclined structure, which controls the angle and thus the sharpness of the needle or blade. Various materials, such as metal, plastic, polymer, and/or biocompatible materials, can be deposited onto a mold structure to create a needle, a needle array, a blade or a blade array for a specific application.

In certain embodiments, also provided are devices including needles, blades, microneedle arrays, and microblade arrays, wherein the sharpness of the needle or blade is controlled by at least one inclined structure. The device provided by the invention can be of any size, in either length or diameter, and/or of various shapes.

DETAILED DESCRIPTION OF THE INVENTION

A beveled metallic needle is developed using a three-dimensional ("3D") SU-8 mold structure. Microneedle array with controllable beveled angle of the needle tip in metal, plastic and other materials can also be made. The 3D mold is fabricated using an angled exposure onto the SU-8 to create a skewed surface which will become a beveled surface followed by a series of vertical exposures to create wells which will then become needle posts. Development of various depths with a single exposure is a crucial factor for creating a mold structure with a beveled surface. Similar fabrication procedures can be adopted to create a blade or micro-blade. The invention provides complex design for controllable 3D tip geometry.

Existing microneedle fabrication techniques cannot control the needle tip geometry in 3D. Some existing techniques can produce an angled needle. However, the present invention offers far more flexibilities. For example, the present invention can provide a tubular hollow needle with an angled tip. The present invention can also provide controlled sharp needle tip or other 3D geometries for various purposes such as easy penetration for drug delivery, blood and/or cell extraction, cell manipulation or transfer, etc. A 3D knife blade with controlled blade can also be created for microsurgical applications. The fabrication can be carried out in either a vertical or a horizontal layout.

In one aspect, the invention provides a method for preparing a needle with or without a hollow section, a needle array, a blade or a blade array, the method comprising: creating at least one inclined or skewed structure that defines the angle of the needle or blade tip. The inclined structure can be created by various techniques including but are not limited to mechanical machining, laser ablation, lithography, abrasion, electric discharged machining (EDM), electric chemical machining (ECM), and etching. Multiple exposures can be used for creating the inclined structure. The inclined structure can be made of various materials. A mold structure or an actual needle (array) or blade (array) structure can be built upon the inclined structure.

Figure 3:
FIG. 3: A schematic of a microneedle manufacturing process: a) a glass substrate, b) metal layer deposition, c) a positive photoresist deposition, d) patterning the photoresist for etching the metal layer, e) spin-coating SU-8 photoresist, f) back-side exposure to create tilted posts, g) spin-coating SU-8 and patterning for needle mold structures, h) developing but not post-exposure bake, i) spin-coating another SU-8 layer for extending post and creating a base, j) developing and performing post-exposure bake, k) depositing a seed layer, l) nickel electroplating, and m) CMP to open the end of the needle base and remove SU-8.
Figure 3:
Figure 3:
Figure 3:
Figure 3:
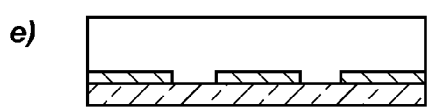
Figure 3:
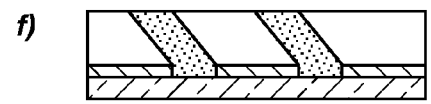
Figure 3:
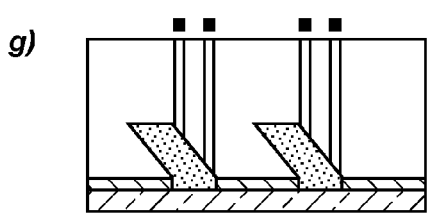
Figure 3:
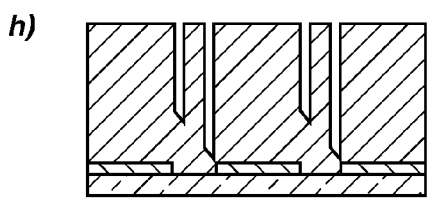
Figure 3:
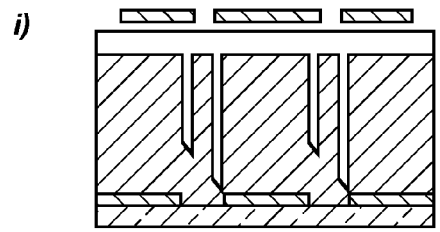
Figure 3:
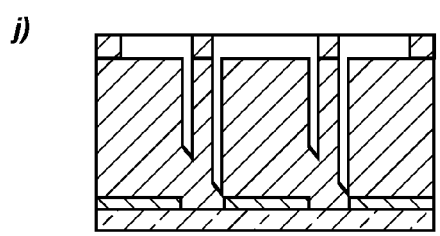
Figure 3:
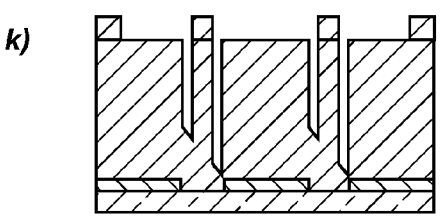
Figure 3:
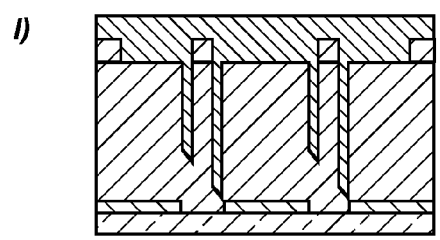
Figure 3:
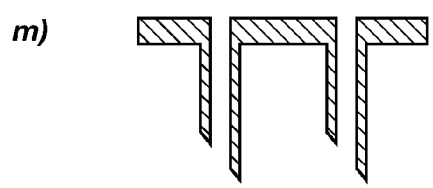

In one embodiment, the mold structure comprises a well with a post inside the well, which well defines a part of the needle wall, and which post defines a part of the hollow section of the needle. A layer of material deposited upon the mold structure becomes a part of the needle wall. A specific example of the present invention is illustrated in FIG. 3(*a*) through (*m*). The present embodiment should be deemed more general than illustrated in FIG. 3. In another embodiment, the mold structure comprises a well without a post inside, applying a layer of material upon the mold structure results in a needle without a hollow section, or a blade.

Figure 12:
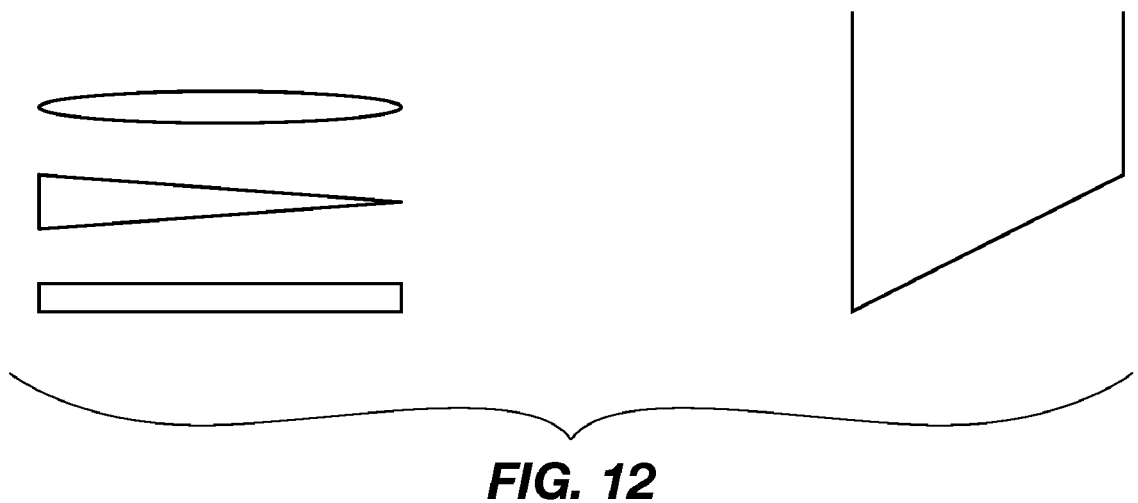
FIG. 12: Various cross sections of a blade or a mold and a side view of a needle structure or mold.

It is to be noted, the masks for patterning a needle or blade (mold) structure, as exemplified in FIG. 3(*g*), can be of various shapes, such as oval, square or diamond. Using different shaped masks thus produces needles or blades of various cross sections, as exemplified in FIG. 12. In order to function as a blade effectively, the cross section of the mold is more likely stretched in one direction than the other. In a particular embodiment, a gray scale mask, as exemplified in FIG. 14(*d*), is used to create a tapered needle or blade structure. A gray scale can also be used for controlling or varying exposure dosage of light sources.

The inclined structure or inclined post that defines the angle of a needle or blade tip can be built upon a substrate. The inclined post may have various angles relative to the substrate, thus providing a needle or blade tip with various angles, and thus providing a needle or blade tip with varying sharpness. A more skewed post will provide a flatter needle tip. A skewed post is exemplified in FIG. 3(*f*). The post can be made of a photoresist material. For example, a negative photoresist such as SU-8 is deposited onto a substrate. The backside of the substrate is exposed under UV light at a desired angle, and then the SU-8 layer is developed in an appropriate bath. The angle of the post relative to the substrate is defined by the direction of the UV irradiation. Such deposition, irradiation and development techniques of photoresist are commonly known in the art of lithography or photolithography. More specifically, a post-exposure bake can be performed. After development of the photoresist layer, a rinse step, e.g., rinsing with isopropyl alcohol, can be applied to check the degree of development and remove uncrosslinked photoresist. Treatment procedures of photoresist such as baking or rinsing are also known in the art. It is also known in the art that photoresist can be patterned by other light sources such as laser and X-ray. A point light source, e.g., laser, can be used to irradiate, at a defined angle, a defined area, as exemplified in FIG. 16.

The substrate, which the inclined post is built upon, can be transparent to a light source. For example, the substrate can be glass or plastic. In one embodiment, a UV-transparent substrate is coated with a non-UV transparent material, such as a metal layer, e.g., chromium. The coated substrate is patterned to create areas that are UV transparent. Patterning of the coated substrate can be facilitated by a layer of photoresist. Patterning techniques of a substrate or a photoresist layer are known in the art, and are exemplified as follows. A positive photoresist, such as AZ 1518, is deposited onto a metal-coated substrate. The substrate is baked and exposed to UV light under a patterned mask. The patterned photoresist is developed, and then the surface of the metal-coated substrate is etched to define a mask to be used for creating an inclined post that defines the tip angle of a needle. An example of patterning a metal-coated substrate is illustrated in FIG. 3(*a*) through (*d*). In another embodiment, when a UV-transparent substrate is used, a patterned mask can be placed under the substrate to facilitate UV exposure from the backside, and thus coating of the substrate with a non-UV transparent material is not necessary.

However, the substrate needs not to be transparent to a light source. For example, one can expose a photoresist layer deposited on a substrate from the top with a light source set at an appropriate angle to produce an inclined post, as exemplified in FIG. 14(*a*).

It should be appreciated, in various embodiments of the invention, when a certain structure is obtained, regardless of the shape and/or material the structure is built of, a layer of material, such as an elastomer, can be applied upon this original structure to produce a negative or a mold of the original structure, which layer of material fills the cavity of the original structure. In addition, a sacrificial mold structure can be obtained by applying a solvent soluble material over a replicated elastomer structure. An example for such a solvent soluble material is PVA.

Figure 15:
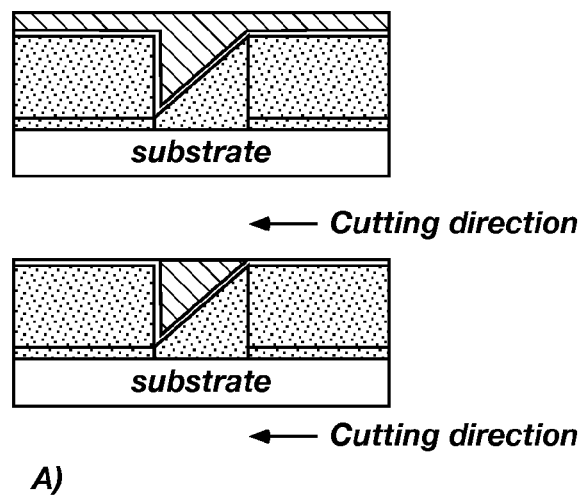
FIG. 15: Designs for blade and blade mold structures.
Figure 15:
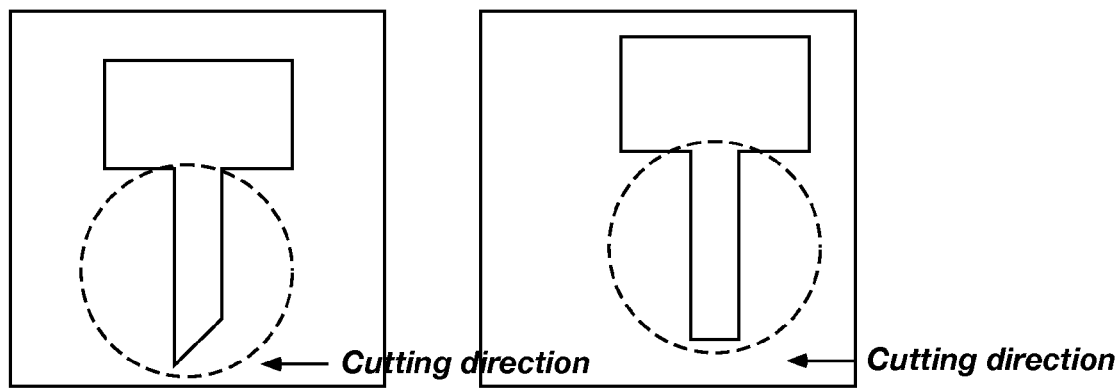

The inclined post can be in a vertical position, as exemplified in FIG. 3, or in horizontal position, as exemplified in FIG. 15(A). It should be appreciated that, in certain cases, one inclined structure is required to create a sharp edge or tip, as exemplified in FIG. 15(B)(*b*). In some other cases, at least two inclined structures are needed to form a cutting edge of a blade, as exemplified in FIG. 15(B)(*a*).

A blade or needle mold structure can be built by depositing a layer of photoresist, such as SU-8, on the inclined post. The thickness of this layer defines the length (height) of the needle or blade. Therefore, the thickness of this layer of photoresist may be adjusted to obtain a needle or blade of desired height. This layer of photoresist can be patterned with UV exposures, resulting in a well with a post inside the well. FIG. 3(*g*) shows an example of patterning of a photoresist material with UV exposure. The well and the post provided by this layer of photoresist are exemplified in FIG. 3(*h*). The post provided by this layer will become a part of the hollow section of a needle. The well provided by this layer defines the needle wall. It is to be noted that patterning of this layer of photoresist material can create a well of various shapes or sizes, thus providing a needle with a wall of various shapes or thickness. Also, patterning of this layer can create a needle with variously shaped post, thus creating variously shaped hollow section, although a needle with a cylindrical hollow section is preferred and practical. Such patterning techniques to create a well and a post of various sizes or shapes are well known in the art of lithography. Prior to UV irradiation, this layer of photoresist may be soft-baked.

Consequently, a layer of photoresist material, such as SU-8, is deposited upon the well with a post inside, which post defines the hollow section of the needle and which well defines the needle wall. This layer of photoresist can be patterned resulting in an extended post in the well, and creating a base for the needle. An example of creating the extended post and the needle base is illustrated in FIG. 3(i) and (j). This layer of photoresist may be soft-baked prior to UV irradiation and/or baked after UV irradiation. Then a development step is performed to obtain a mold structure, namely, a well with a (extended) post inside the well.

Appropriate materials can be deposited upon a mold structure to form a needle or a blade. Such materials may be metal, such as nickel, palladium, stainless steel, and/or other materials such as polymers and ceramics. The mold structure can be removed to obtain the needle. Deposition of a metal upon a mold structure can be carried out by electroplating. Prior to electroplating, a seed layer may be deposited onto a mold structure. After electroplating, chemical polishing may be used to remove access electroplated material. An example of depositing a seed layer, electroplating and opening the needle base is illustrated in FIG. 3(k) through (m).

It is to be noted that a person skilled in the art can make modifications to the methods as described. For example, a person skilled in the art can make modifications to the disclosed mold structure thus fabricate a mold structure comprising a well without a post inside. Applying a material upon the mold structure results in a needle without a hollow section, or a blade. For another example, a blade of an arbitrary shape, such as a die cutter, can be created following similar principle and/or procedures. As well, the sequences of the procedures in various embodiments of the invention can be changed. It is also to be noted that the method described can provide an array of inclined structures, thus providing a needle or blade array mold structure, and thus providing a needle array, a microneedle array, a blade array or a microblade array.

It will be appreciated that a process for producing a needle or blade structure may comprise a process of creating a mold structure. For example, in FIG. 3, the process for creating a needle mold comprises steps (a) through (k). Consequently steps (l) and (m) produces a needle structure built upon the mold. However, once a needle structure is obtained, a negative mold can be easily built by applying a layer of material, such as elastomer, over the needle or blade structure. An example of such elastomer is PDMS. Obtaining a mold structure by applying an elastomer over an actual needle structure is exemplified in FIG. 13.

In another aspect, the invention provides a mold structure that facilitates fabrication of a needle, a needle array, a blade or a blade array. Such a mold structure can be built by various embodiments of the method disclosed. In one embodiment, a mold structure is built upon at least one inclined structure, which controls the angle of the needle or blade tip. A needle mold may comprise a well with a post inside the well, which well defines a part of the needle wall, and which post defines a part of the hollow section of the needle. A specific example of a needle mold is illustrated in FIG. 3(h) through (j). The need or blade mold provided by the present invention should be deemed more general than illustrated in FIG. 3(h) through (j). A blade or needle mold structure may comprise a well without a post inside, which well defines part of the blade or needle body.

In certain embodiments, provided are devices including needles, blades, needle arrays, microneedle arrays, blade arrays and microblade arrays, wherein the angle or sharpness of the blade or needle are controlled by at least one inclined structure. A device provided herein can be of any size, in either length or diameter. By varying the patterning of exposures, devices of various shapes can be obtained. Various materials, such as metal, plastic, polymer, and/or biocompatible materials, can be deposited onto a mold structure to create a needle or a blade for a specific application. The devices can be used in drug delivery, sample collection, surgical settings and other areas. Microneedles (or micropipettes) can be used as a component in biomedical diagnostic devices for drug delivery, blood extraction, or transport. Microblades can be used in surgical devices that require micro-scale blade. Arrays of microneedles or microblades can be used for high throughput screening or diagnostic assays, and other far reaching yet not foreseeable applications.

The present invention is further described in the following non-limiting examples, which are offered by way of illustration and are not intended to limit the invention in any manner.

EXAMPLES

Example 1

Creation of Sharp Metallic Microneedles and Microneedle Arrays

A new manufacturing method to create a beveled metallic microneedle is introduced. The method uses a side wall surface of an angled post as a base for the needle tip to create the beveled tip geometry for easy skin penetration. With proper dimensional corrections, the microneedle manufactured using the present method allows to keep the strength of the needle structure while increasing skin penetration ability since the cross-section area of the needle post structure is not required to sacrifice. Therefore, the microneedle provided by the present method can be used in clinical practice providing a safe and painless administration, but without potential concerns.

Construction of angled structures using inclined exposure fabrication technique is available for many applications, e.g., microfilter, microchannel, microstructures, etc.[16-23] The first fabrication step for a microneedle was performed with backside exposure on a layer of SU-8. On a patterned metal layer coated on a glass substrate, SU-8 was applied and exposed from the back to create inclined post. The angle of the post is then used to determine the angle of the microneedle structure. Since the UV light travels through air, glass, and SU-8 in sequence, the range of the angle governed by Snell's law as below.

$$\frac{Sin\Theta_1}{n_2} = \frac{Sin\Theta_2}{n_1} \tag{2.1}$$

Figure 1:
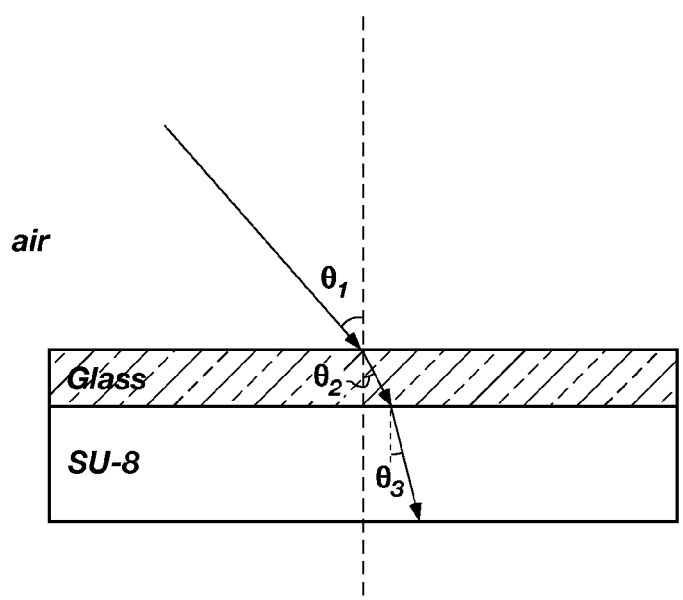
FIG. 1: A schematic of light angles traveling through a limestone glass substrate. $\Theta_1$ and $\Theta_2$ are incident angles for the glass substrate and SU-8. $\Theta_3$ is the refractive angle in SU-8.
Figure 2:
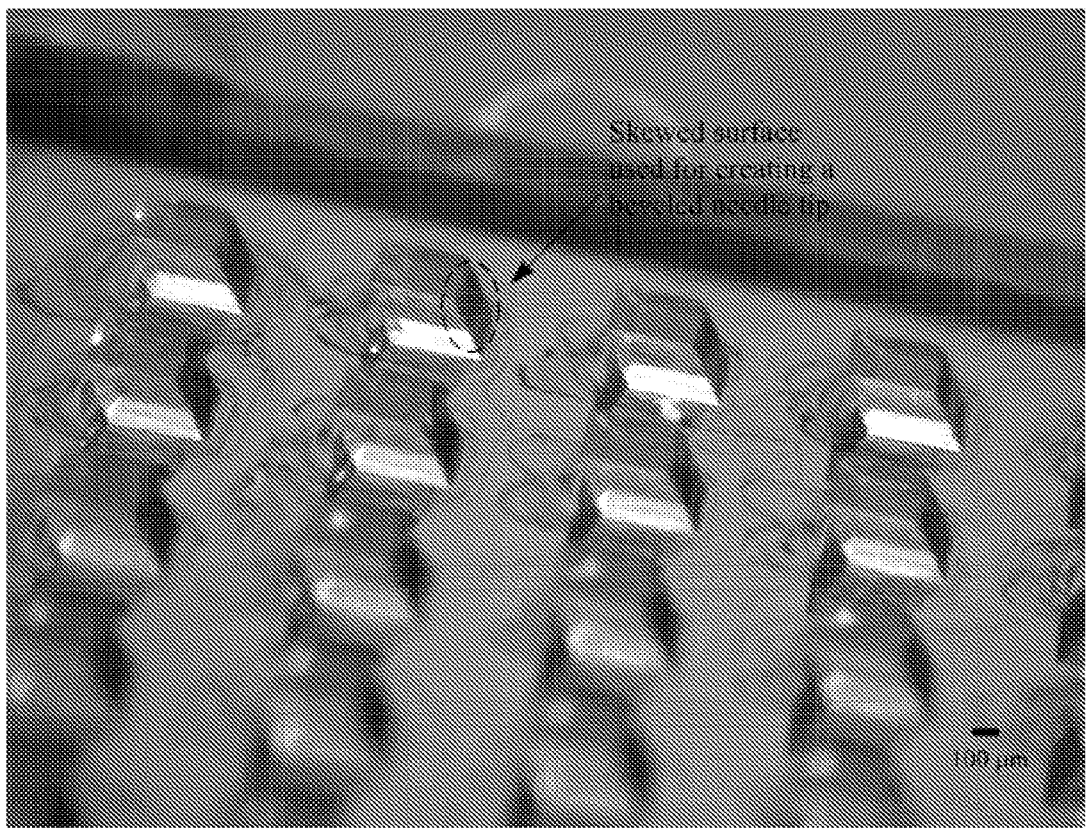
FIG. 2: An array of skewed posts.

Where, $\Theta_1$ and $\Theta_2$ are the incident and refractive angles, respectively, $n_1$ and $n_2$ are the refractive index of the medium where the light is entering and leaving, respectively. According to Snell's law, the incident angle of the UV light that travels through the SU-8 layer is determined by the refraction index of the glass substrate. To determine the incident angle of the light at the interface between SU-8 and the glass substrate, the refraction index used for the glass and SU-8 were approximately 1.52 and 1.67 at 365 nm wave lengths, respectively. From this, the range of the refracted light that can be used to define the beveled angle on the tip of the microneedle should be about between 0 to 36.78 degrees. FIG. 1 shows the paths of the light traveled through the all three mediums and Table 1 shows the range of angles for the beveled microneedle tip that can be obtained from SU-8 in every 10 degrees of incident angles of air. The calculated angles for the glass are used for incident light angles of the SU-8. FIG. 2 shows the actual skewed post fabricated during the microneedle manufacturing.

TABLE 1

Approximate beveled angle range of the microneedle

| air* | glass* | SU8* |
|---|---|---|
| 0 | 0 | 0 |
| 10 | 6.55991952 | 5.9684576 |
| 20 | 13.0036574 | 11.817937 |
| 30 | 19.2048975 | 17.421641 |
| 40 | 25.0169643 | 22.637704 |
| 50 | 30.2634408 | 27.303849 |
| 60 | 34.7330422 | 31.236921 |
| 70 | 38.1861803 | 34.242047 |
| 80 | 40.3834451 | 36.136094 |
| 90 | 41.1395104 | 36.784174 |

*Angles in degrees

Refractive index for air, glass, and SU-8 is 1, 1.52, and 1.67, respectively.

Therefore, patterning of any tube geometries on top of the side wall surface of the inclined post which faces upward allows creating a beveled surface on the bottom of the microneedle mold structure. This bottom surface later becomes the beveled surface of the microneedle structure.

Figure 4:
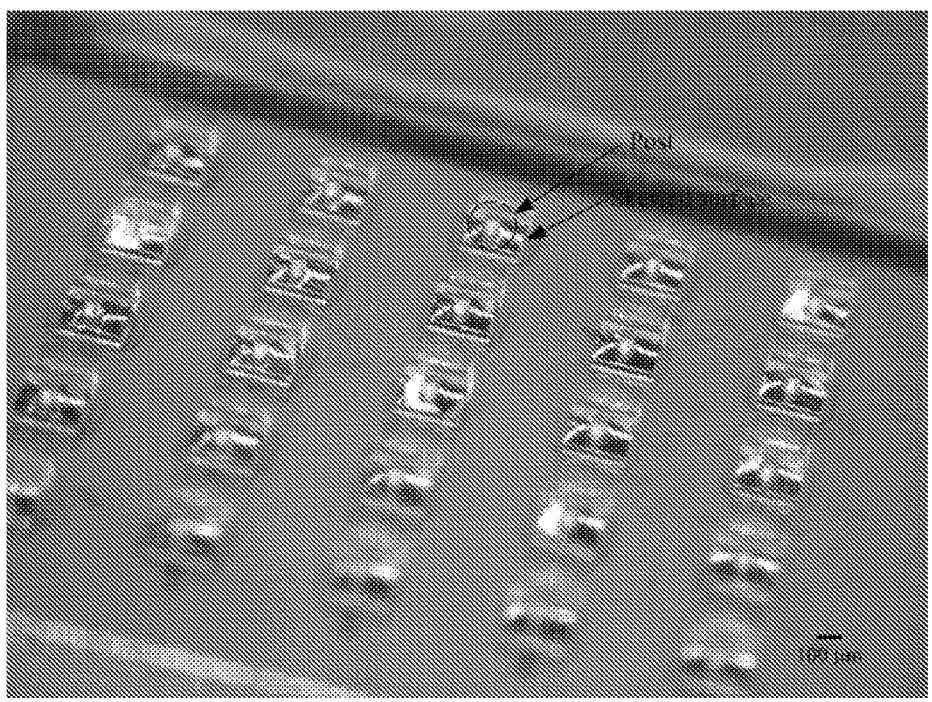
FIG. 4: An example of inside structures of wells.
Figure 5:
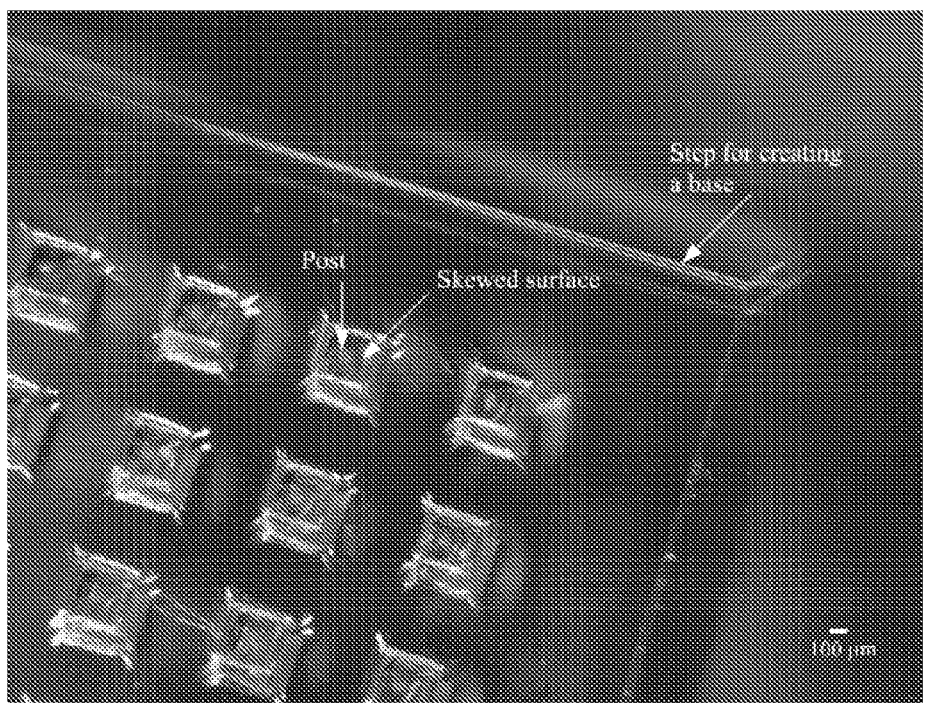
FIG. 5: An array of wells before electroplating.
Figure 6:
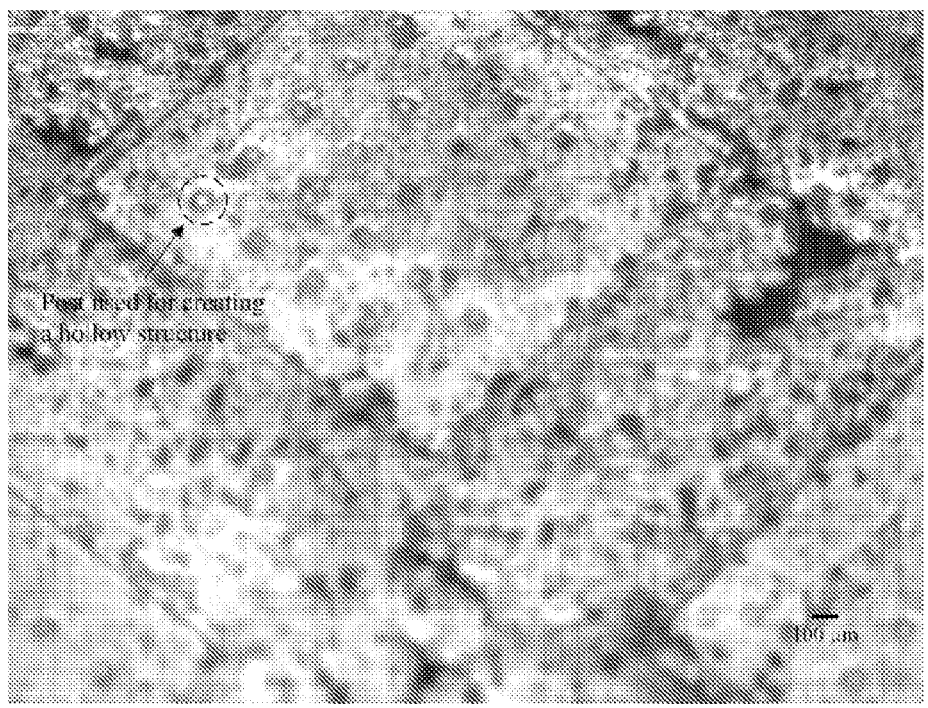
FIG. 6: A picture showing posts used for creating hollow structures during electroplating for a microneedle array.

The fabrication procedures to create an out of plane metallic beveled microneedle are illustrated in FIG. 3. There are four major microneedle manufacturing stages. FIG. 3(a) to (f) shows the first manufacturing stage described as following. The manufacture begins as performing a metal layer deposition, Chromium (Cr), of about 0.1 μm on a limestone glass substrate using a Denton discovery 18 sputtering system. A positive photoresist (AZ 1518) is then spun onto the metal layer for patterning square arrays after baking and exposing it under the Ultra Violet (UV) light. Developing patterned photoresist followed by etching the metal layer defines a mask to be used for creating the array of skewed posts. SU-8 (2075), a negative photoresist, is then spin-coated on the patterned metal layer at 500 rpm with acceleration of 100 rpm/s for 10 seconds followed by spinning at 1200 rpm with acceleration of 300 rmp/s for 30 seconds to obtain about 150 μm in thickness. Next, the substrate is soft-baked on a hotplate at 65° C. for 3 minutes followed by baking at 95° C. for 22.5 minutes. After cooling it down to the room temperature, the backside of the substrate is exposed under UV light with a dose of about 400 mJ/cm² at a tilted angle of 55 degrees using Kasper Instruments mask aligner. A post exposure bake is performed at 65° C. for 3 minutes and 95° C. for 15 minutes. The SU-8 layer is developed in a bath with a stirrer spinning at 700 rpm to enhance developing rate for 25 minutes. The SU-8 layer is rinsed with isopropylalcohol (IPA) to check the degrees of development and remove uncrosslinked photoresist. The substrate is dried with a nitrogen gas to prepare for the next manufacturing steps of which the microneedle structures will build on top of the array of the skewed posts (FIG. 3(g) to FIG. 3(i)). The second layer of SU-8 is then carried out to spin-coat over the skewed post arrays at 300 rpm with acceleration of 100 rpm for 10 seconds and spin at 630 rpm with acceleration of 500 rpm/s for 30 seconds to obtain about 270 μm in thickness. FIG. 3(g) shows the cross-section of the patterned geometry in which the dimensions of the outside and inside diameter of 370 μm and 70 μm, respectively, were used for the current experiment. It is noted that the thickness of this layer becomes the length of the microneedle. This second SU-8 layer is soft-baked on the hotplate at 65° C. for 3 minutes and 95° C. for 5 hours and patterned with arrays of wells with a post in the middle in each well using Electronic Visions EV-420 with a dose of 550 mJ/cm². An example of how the post looks like inside of the well can be seen in FIG. 4. FIG. 4 shows that the configuration of the interface between the angled surface and the cylindrical post, which post will be used for creating the hollow section of the microneedle. Now, the third manufacturing step (FIG. 3(j) to (k)) starts without post-exposure baking the second SU-8 layer, but spin-coating the third SU-8 layer over the third layer at 500 rpm for 10 seconds and 1600 rpm to obtain 100 μm. The purpose of this step is to extend the post in the middle of the well as well as to define the base for the entire 5×5 microneedle array. Soft-bake of the third layer on a hotplate results in the second SU-8 layer becoming cross-linked in addition to removing solvents from the third layer. Exposing the layer with a dose of 350 mJ/cm² and post-bake are performed to cross-link the polymer layer at 65° C. for 3 minutes and 95° C. for 22.5 minutes. Next step is to develop the second and third layers for 1 hour in the bath with a stirrer rotating at 700 rpm. FIG. 5 shows an array of wells with a post in the middle of each well created after development. Finally, the last manufacturing step is to create the metallic microneedle array (FIG. 3(l) to (m)). The array of wells is subject to sputter to deposit a seed layer for electroplating. Nickel sulfamate bath is then prepared for nickel electroplating to deposit nickel about 500 μm thick. A selection of metal includes biocompatible materials such as palladium, stainless steel, etc. in practice. After nickel electroplating, Chemical Mechanical Polishing (CMP) is carried out to remove access material on the top surface of the nickel until SU-8 posts are exposed. FIG. 6 shows the picture of the protruded SU-8 posts inside of the microneedle base during the electroplating process. Removing the mold structure made of SU-8 is the final step to obtain a beveled metallic microneedle.

Figure 7:
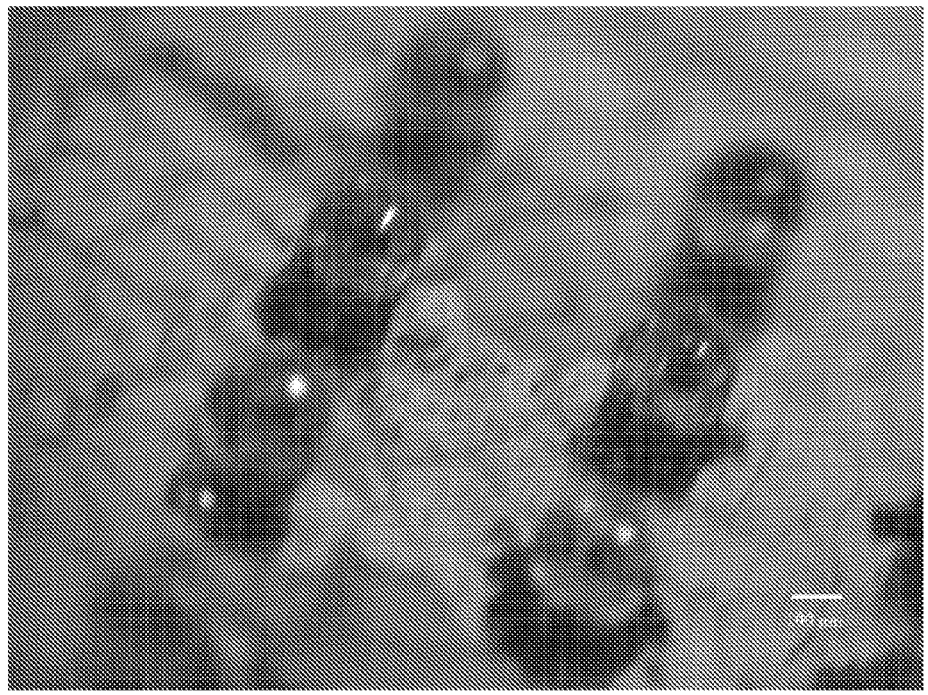
FIG. 7: The front view of a beveled metallic microneedle.
Figure 8:
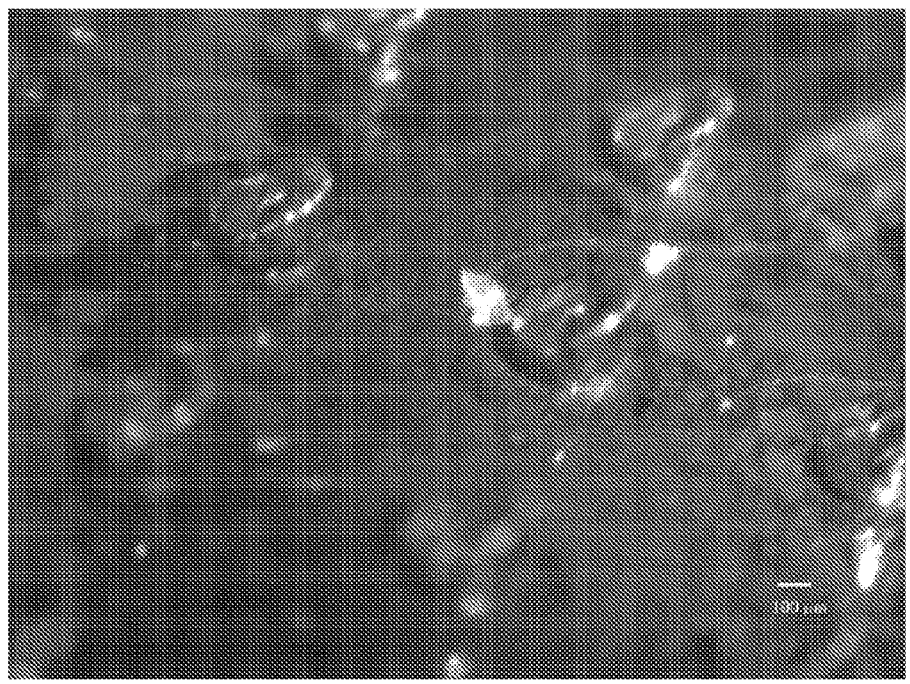
FIG. 8: An angled view of a beveled metallic microneedle.

The most critical aspect of creating a microneedle with the proposed design method depends on the results from the lithography to create SU-8 mold geometry for electroplating. Especially, the sharpness of the needle tip is determined by how well SU-8 is developed and thus creating fine corner geometry. The final product of a microneedle array fabricated using the proposed manufacturing method after removing SU-8 layers are shown in FIGS. 7 and 8. The microneedle structures made of nickel in these pictures are formed with round post mold geometry. The tip angle shown in the figures is about 35° although the edges of the tip looks like somewhat rounded. The roundness is due to the tip geometry in the bottom of the SU-8 mold which was not well developed. Moreover, the surface of the microneedle array is neither clean nor smooth. The uncleanness and roughness come from the left over of SU-8 particles and craze of SU-8 mold surface resulted from the thermal stress during the curing of SU-8 polymer layer.

Figure 9:
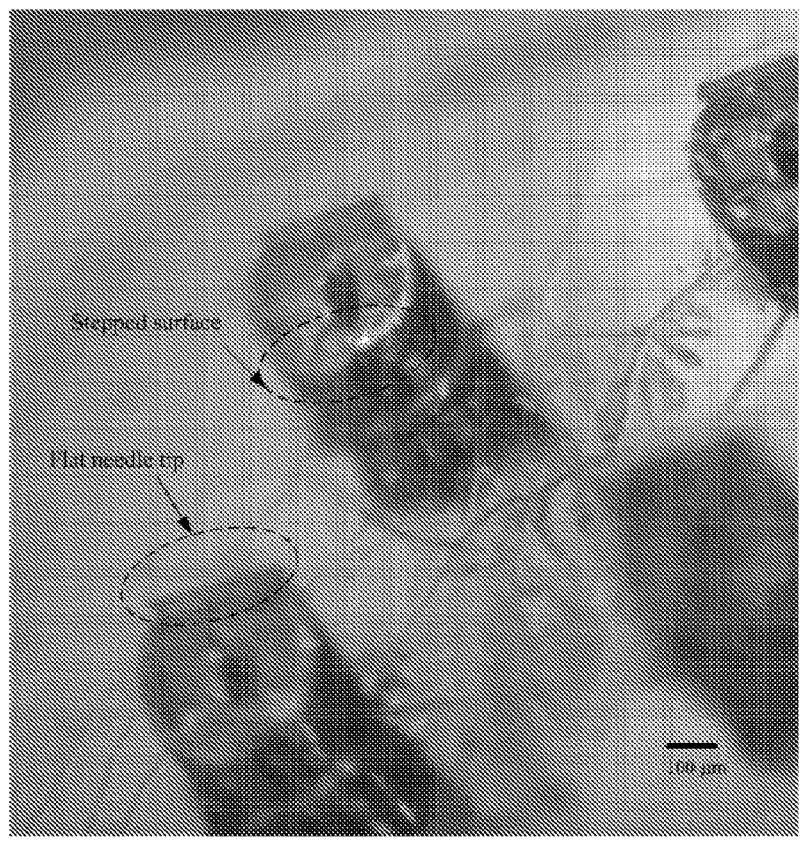
FIG. 9: A round microneedle post with a flat tip.

FIG. 9 shows the microneedle array with a flat tip surface resulted from misalignment during the lithography process. Since the proposed manufacturing method requires three SU-8 layers to complete the molding process, the alignment of each layer determines the quality of final product.

Figure 10:
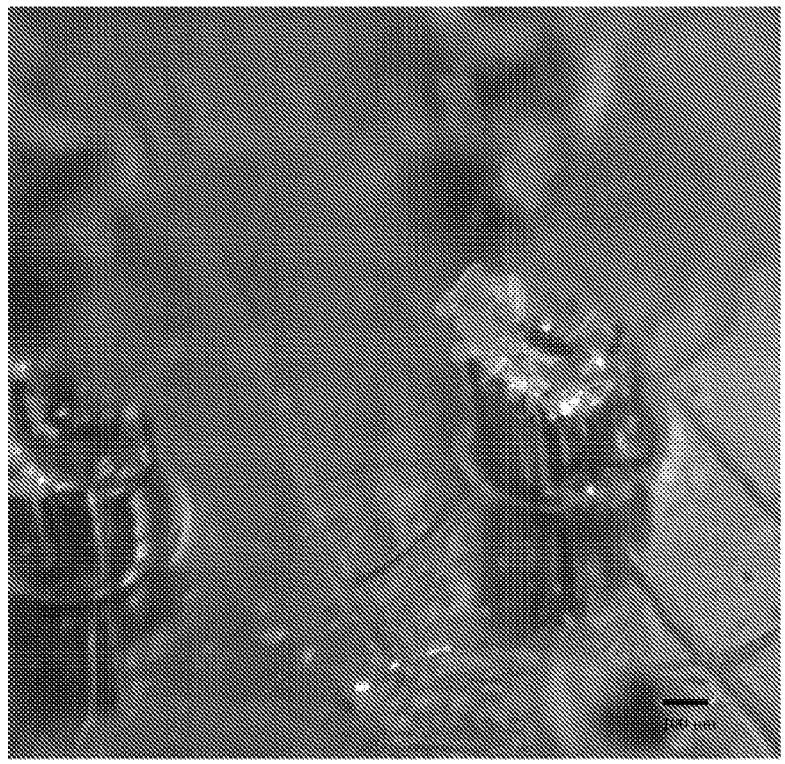
FIG. 10: An angled view of round microneedle post array.
Figure 11:
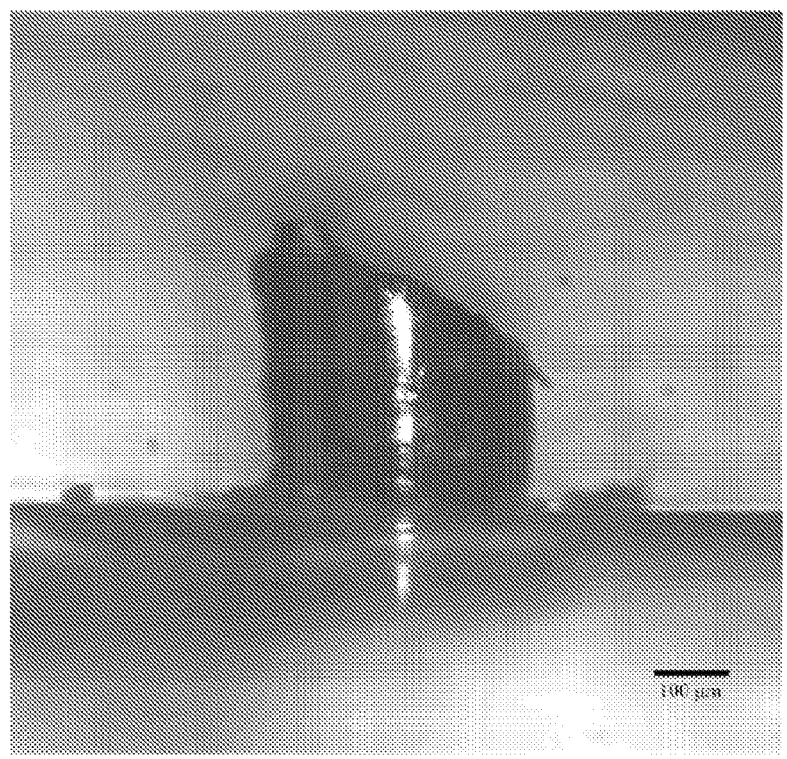
FIG. 11: A backside view at 45 degree angle of round microneedle post.

An angled view of microneedle with round post can be seen in FIG. 10 and backside of its needle post can be seen in FIG. 11.

The advantage of using the new manufacturing method for creating a microneedle is that it gives the freedom of changing the angle of the needle tip in microneedle design without scarifying the needle post strength for easy skin penetration. In addition, there is a potential use of the proposed manufacturing method such that various needle tip geometries can be achieved with multiple exposures during the fabrication of the skewed post.

Example 2

Design of Microneedles and Microneedle Arrays

Figure 13:
FIG. 13: One design for creating microneedle and microneedle mold structures.
Figure 13:
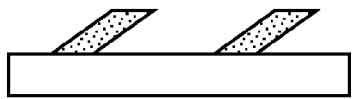
Figure 13:
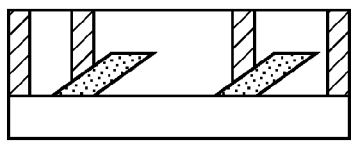
Figure 13:
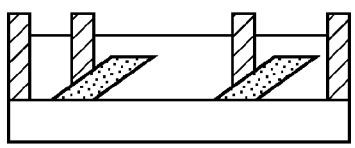
Figure 13:
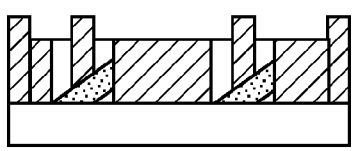
Figure 13:
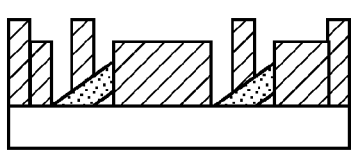
Figure 13:
Figure 13:
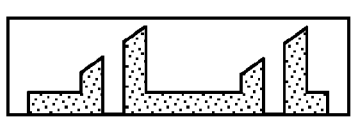
Figure 13:
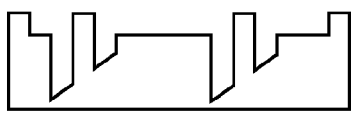

Microneedles and microneedle arrays can also be designed as shown in FIG. 13. A substrate is spin-coated with a layer of photoresist, softbaked and exposed to a light source. After post exposure bake, the photoresist is developed resulting in an inclined post that defines the needle tip. Another layer of photoresist is spin-coated, softbaked and partially exposed to create a base and a post that defines the hollow section of a needle. The photoresist is partially developed to expose the base and the post that defines the hollow section of the needle. The photoresist is exposed partially to the light source to create boundaries of the needle structure. After post exposure bake, the entire mold structure is developed. A seed layer is deposited onto the mold structure and a metal layer is electroplated. Alternatively, the seed layer may be deposited right after the inclined post is created. Chemical mechanical polishing opens the hollow area of the needle. The mold structure is removed to obtain the final needle structure. A layer of elastomer, e.g., PDMS, is cast over the actual needle structure and therefore, a mold made of PDMS is obtained.

Example 3

Design of Tapered Microneedles and Microneedle Arrays

Figure 14:
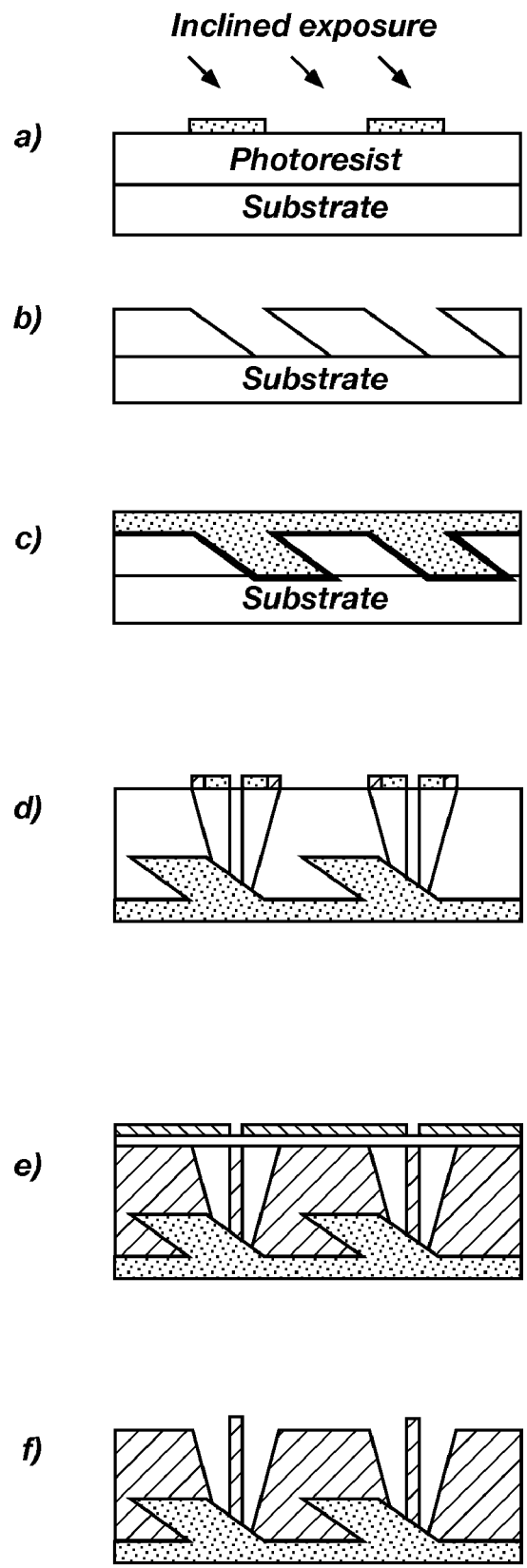
FIG. 14: One design for tapered microneedle and microneedle mold structures.

Tapered microneedles and microneedle arrays can be created as shown in FIG. 14. A negative photoresist is coated on a substrate, softbaked, and exposed under UV light with an inclined exposure. After post exposure bake and development, the photoresist is coated with a mold release agent or a sacrificial layer for easy release of an elastomer layer (e.g., PDMS). An example for such a mold release agent is a fluorosilanizing agent. An elastomer is cast upon the mold release agent or the sacrificial layer to obtain an elastomer structure, which is then used as a base for further construction.

The elastomer base is coated with a layer of negative photoresist (e.g., SU-8) for creating a needle or needle array mold structure. The negative photoresist is softbaked and exposed with a given photomask positioned on the negative photoresist. To create tapered geometry, a gray scale mask can be used. Alternatively, adjusting diffraction of the light can also produce similar geometry.

Another layer of SU-8 is spin-coated without developing the previous layer. The entire layers are softbaked, exposed and post exposure baked. Alternatively, calculated dosage can be used for exposing only the second SU-8 layer. Development of the layers results in a SU-8 mold structure. A layer of material, such as metal, can be cast upon the mold structure and therefore produce an actual needle structure.

This example shows that a replicated angled structure, such as the one made of PDMS, can be used a base for fabricating a microneedle.

Example 4

Design of a Die Cutter

Figure 16:
FIG. 16: One design for a die cutter.
Figure 16:
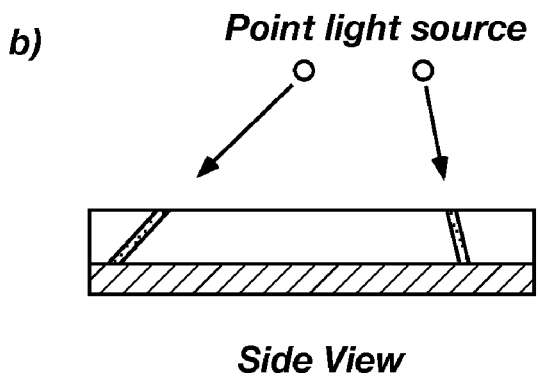
Figure 16:
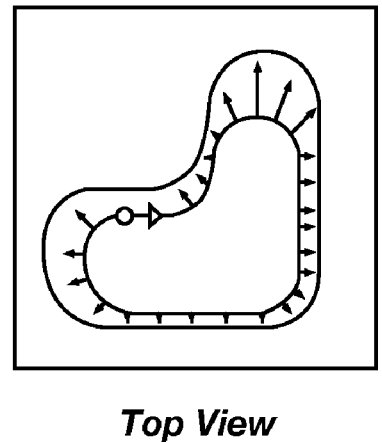
Figure 16:
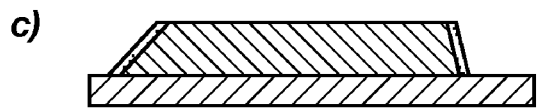
Figure 16:
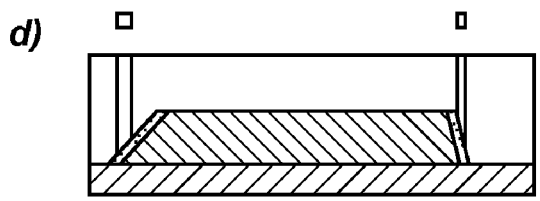
Figure 16:
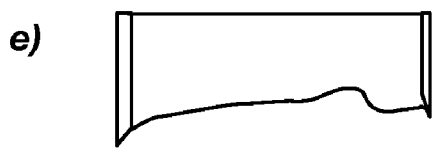

A die cutter can be created as shown in FIG. 16. A photoresist layer is spin-coated on a substrate. Point light sources, such as laser, write directly on the photoresist at a defined angle. An arbitrary inclined shaped structure is obtained after developing the photoresist. A layer of photoresist is spin-coated on the arbitrary shaped structure. The blade 2D top layout is patterned using a mask or by direct writing. After the photoresist is developed, the cavity can be filled with a material such as ceramics. Removal of the photoresist mold to obtain a die cutter. A metal cutter can also be obtained by electroplating.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

REFERENCES

[1] Y. F. Tsai and P. C. Hsiung, "Aboriginal Nurses Perception of Facilitators and Barriers for Taking a Sexual History in Taiwan," *Public Health Nursing*, v20, n4, 2003, pp 281-286.

[2] J. Jagger and J. Perry, "Preventing Sharps Injuries in the Home," *Nursing*, v30, n12, 2000, p 73.

[3] T. Cole, "Medical Errors vs Medical Injuries," *Journal of the American Medical Association*, v284, n17, pp 2175-2177.

[4] B. Salzberger, W. Wiesel, E. Schwingel, and I. Hauber, "Occupational HIV infection documented by sequence analysis of source and index virus strains," *HIV Medicine*, v1, n4, pp 256-258.

[5] E. A. McConnell, "Infection Control: More Than a Matter of Economics," *Nursing Management*, v30, n6, 1999, pp 64-65.

[6] R. J. Pettis, "Microneedle Based Drug Delivery: A Promising Minimally Invasive Method for Parenteral Administration," *Drug Delivery Report, Technology/Industry Overviews*, 2004, pp 20-23.

[7] D. V. McAllister, P. M. Wang, S. P. Davis, J. H. Park, P. J. Canatella, M. G. Allen and M. R. Prausnitz, Microfabricated needles for transdermal delivery of macromolecules and nanoparticles: Fabrication methods and transport studies, *PNAS*, v100, n24, 2003, pp 13755-13760.

[8] D. V. McAllister, M. G. Allen and M. R. Prausnitz, Microfabricated Microneedles for Gene and Drug Delivery, *Annual Reviews Biomedical Engineering*, 2000, pp 289-313.

[9] B. Stoeber and D. Liepmann, "Arrays of Hollow Out-of-Plane Microneedles for Drug Delivery," *Journal of Microelectromechanical Systems*, v14, n3, 2005, pp 472-479.

[10] J. D. Brazzle, I. Papautsky and B. Frazier, "Fluid coupled hollow metallic microfabricated needle arrays," SPIE Conference on Microfluidic Devices and Systems, Santa Clara, Calif., v3515, September 1998, pp 116-123.

[11] J. D. Brazzle, S. Mohanty, S., and Frazier, A. B., "Hollow Metallic Micromachined Needles with multiple Output Ports," SPIE Conference on Microfluidic Devices and Systems II, Santa Clara, Calif., September 1999, v3877, pp 257-266.

[12] K. Kim, D. S. Park, H. M. Lu, W. Che, K. Kim, J. B. Lee and C. H. Ahn, "A tapered hollow metallic microneedle array using backside exposure of SU 8," *Journal of Micromechanics and Microengineering*, v14, 2004, pp 597-603.

[13] S. S. Lee and S. J. Moon, "A Novel Fabrication Method of a Microneedle Array Using Inclined Deep X-ray Exposure," *Journal of Micromechanics and Microengineering*, v15, 2005, pp 903-911.

[14] S. J. Moon and S. S. Lee, "Fabrication of Microneedle Array Using Inclined LIGA Process," The 12$^{th}$ International Conference on Solid State Sensors, Actuators and Microsystems, Boston, Jun. 8-12, 2003, pp 1546-1549.

[15] S. Kuo and Y. Chou, "A Novel Polymer Microneedle Arrays and PDMS Micromolding Technique," *Tamkang Journal of Science and Engineering*, v7, n2, 2004, pp 95-98.

[16] Y. K. Yoon, J. H. Park, F. Cros, and M. G. Allen, "Integrated Vertical Screen Microfilter System Using Inclined SU-8 Structures," The 17$^{th}$ International Conference of MEMS 2004.

[17] H. Y. Li and X. Zhang, "Flexible Fabrication of Three-dimensional Multi-layered Microstructures Using a Scanning Laser System," *Sensors and Actuators-A physical*, 2006, pp 553-564.

[18] F. Romanato, R. Kumar, and E. D. Fabrizio, "Interface Lithography: a Hybrid Lithographic Approach for the Fabrication of Patterns Embedded in Three-dimensional Structures," *Nanotechnology*, v16, 2005, pp 40-46.

[19] M. Han, W. Lee, S. K. Lee, and S. S. Lee, "Fabrication of 3D Microstructures with Inclined/Rotated UV Lithography," *IEEE*, 2003, pp 554-557.

[20] M. H. Han, W. S. Lee, S. K. Lee, and S. S. Lee, "Fabrication of 3D Microstructures with Single UV Lithography Step," *Journal of Semiconductor Technology and Science*, v2, n4, 2002, pp 268-272.

[21] K. Y. Hung, H. T. Hu and F. G. Tseng, "Application of 3D glycerol-compensated Inclined-exposure Technology to an Integrated Optical pick-up Head," *Journal of Micromechanics and Microengineering*, v14, 2004, pp 975-983.

[22] K. Y. Hung, H. T. Hu, and F. G. Tseng, "A Novel Fabrication Technology for Smooth 3D Inclined Polymer Microstructures with Adjustable angles," The 12$^{th}$ International Conference on Solid State Sensors, Actuators, and Microsystems, 2003, pp 821-824.

[23] H. Sato, T. Kakinuma, J. S. Go, and S. Shoji, "A Novel Fabrication of In-channel 3-D Micromesh structure Using Maskless Multi-angle Exposure and Its Microfilter Application," *IEEE*, 2003, pp 223-226.

[24] D. Sparks and T. Hubbard, "Micromachined needles and lancets with design adjustable bevel angles," *Journal of Micromechanics and Microengineering*, v14, 2004, pp 1230-1233.

[25] F. Perennes, B. Marmiroli, M. Matteucci, M. Tormen, L. Vaccari, and E. D. Fabrizio, "Sharp Beveled Tip Hollow Microneedle Arrays Fabricated by LIGA and 3D Soft Lithography with Polyvinyl Alcohol," *Journal of Micromechanics and Microengineering*, v16, 2006, pp 473-479.

What is claimed is:

1. A method for making at least one implement comprising at least one needle or at least one blade having an angled tip, the method comprising:
    creating at least one inclined structure which defines an angle of the angled tip of the at least one implement, the angle defining the implement's sharpness; and
    building at least one needle mold structure or at least one blade mold structure on the inclined structure.

2. The method according to claim 1, wherein the needle mold structure comprises a well with a post inside the well, which well defines a part of a needle wall of the at least one needle, and which post defines a part of a hollow section of the at least one needle.

3. The method according to claim 1, wherein the at least one needle comprises a needle without a hollow section, and wherein the needle mold structure comprises a well without a post inside the well, which well defines a part of a wall of the needle without a hollow section.

4. The method according to claim 1, wherein the blade mold structure comprises a well without a post inside the well, which well defines a part of a blade body of the at least one blade.

5. The method according to claim 1, wherein the at least one inclined structure is created by mechanical machining, laser ablation, lithography, abrasion, electric discharged machining (EDM), electric chemical machining (ECM), or etching.

6. The method according to claim 1, wherein the at least one inclined structure is created by one exposure, or more than one exposure to a light source.

7. The method according to claim 6, wherein the light source is UV, laser, or X-ray.

8. The method according to claim 1, wherein the mold structure is in a vertical or a horizontal position.

9. The method according to claim 1, further comprising depositing at least one layer of material to the at least one needle mold structure or the at least one blade mold structure, and removing the mold structure to obtain the at least one needle or at least one blade.

10. The method according to claim 9, wherein the material is metal, plastic, ceramic, or photoresist.

11. The method according to claim 1, wherein the implement forms a microneedle array or a microblade array.

12. A method for forming a beveled microneedle, characterized in that the method employs a separate side wall surface of an angled post as a base for a tip of the microneedle to form the beveled microneedle against the separate side wall surface.

13. The method of claim 12, wherein the beveled microneedle is metallic.

14. A method for making a microneedle or a microneedle array, the method comprising:
    coating a glass substrate with a layer of metal;
    depositing a layer of positive photoresist on the metal-coated glass substrate;
    patterning the positive photoresist for etching the metal layer;

etching the metal layer;
spin-coating a first layer of SU-8 photoresist on the etched metal-coated surface;
exposing the substrate on the back-side of the SU-8 to UV at a defined angle to create at least one inclined post;
spin-coating a second layer of SU-8 and patterning for a needle or needle array mold structure;
developing the SU-8, but not post-exposure baking;
coating a third layer of SU-8 for extending at least one post that defines a hollow section of the needle and creating at least one needle base;
performing a post-exposure bake and developing the third layer of SU-8 to obtain a SU-8 needle or needle array mold structure;
depositing a seed layer on the mold structure;
nickel electroplating the mold structure;
applying chemical mechanical polishing (CMP) to open an end of the needle base; and
removing the mold structure to obtain the microneedle or microneedle array.

15. The method according to claim 14, further comprising:
depositing a seed layer onto the mold structure prior to electroplating.

16. The method according to claim 14, further comprising:
depositing a seed layer upon the inclined post after the inclined post is created.

17. A method for making a needle or a needle array, the method comprising:
spin-coating a substrate with a first photoresist;
softbaking the first photoresist;
exposing the first photoresist to a light source at a defined angle;
post exposure baking the first photoresist if necessary;
developing the first photoresist to obtain at least one inclined post that defines a needle tip;
spin-coating a second photoresist;
softbaking and exposing the second photoresist to create at least one base and at least one post that defines a hollow section of the needle;
partially developing the second photoresist to obtain the base and the post that defines the hollow section of the needle;
exposing the second photoresist to a light source to create boundaries of a needle or needle array mold structure;
post exposure baking the second photoresist if necessary;
developing the mold structure;
electroplating a metal layer onto the mold structure;
applying CMP to open the hollow section of the needle; and
removing the mold structure to obtain the needle or needle array.

18. A method for making a blade cutter of an arbitrary shape, the method comprising:
spin-coating a first photoresist on a substrate;
writing a point light source on the first photoresist at a defined angle;
developing the first photoresist;
spin-coating a second photoresist;
patterning a top layout of the blade cutter using a mask or by direct writing of the light source;
developing the second photoresist to obtain a cutter mold structure;
applying a material to the mold structure; and
removing the mold structure to obtain the blade cutter.

19. The method of claim 18, wherein the point light source is a laser.

20. A method for making a needle or a needle array, the method comprising:
coating a first negative photoresist on a substrate;
softbaking the first photoresist;
exposing the first photoresist under UV light with an inclined exposure;
post exposure baking the first photoresist if necessary;
developing the first photoresist to obtain at least one inclined post;
coating the at least one inclined post with a mold release agent or a sacrificial layer;
applying an elastomer upon the mold release agent or the sacrificial layer to obtain an elastomer structure;
disassociating the elastomer structure from the mold release agent or the sacrificial layer so as to apply the elastomer structure as a base for further construction of the needle or needle array;
coating the elastomer structure with a second negative photoresist for creating a needle or needle array mold structure;
softbaking the second photoresist;
exposing the second photoresist with a given photomask positioned on the second photoresist;
spin-coating a third negative photoresist without developing the second photoresist;
softbaking, exposing, and, if post exposure baking is required, post exposure baking the second and the third photoresist;
developing the second and the third photoresist to obtain a needle or needle array mold structure;
depositing a layer of material upon the mold structure; and
removing the mold structure to obtain the needle or needle array.

21. The method according to claim 20, wherein the photomask is a gray scale mask and wherein the needle or the needle array has a tapered structure.

22. The method according to claim 20, wherein the first, the second, and the third photoresist are SU-8.

* * * * *